United States Patent [19]
Sakamoto et al.

[11] Patent Number: 5,304,467
[45] Date of Patent: Apr. 19, 1994

[54] DEVICE FOR ASSAY OF LIQUID SAMPLE

[75] Inventors: Hisashi Sakamoto, Yawata; Shigeki Yamada, Joyo; Hiroshi Taniguchi, Kyoto, all of Japan

[73] Assignee: Kyoto Daiichi Kagaku Co., Ltd., Kyoto, Japan

[21] Appl. No.: 809,253

[22] Filed: Dec. 18, 1991

Related U.S. Application Data

[63] Continuation of Ser. No. 675,049, Mar. 25, 1991, abandoned, which is a continuation of Ser. No. 442,635, Nov. 29, 1989, abandoned.

[30] Foreign Application Priority Data

Nov. 30, 1988 [JP] Japan .................. 63-157143[U]

[51] Int. Cl.$^5$ .................. G01N 31/22; C12Q 1/28; C12Q 1/54; C12Q 1/62
[52] U.S. Cl. .................. 435/14; 422/57; 422/58; 435/16; 435/21; 435/26; 435/28; 435/805; 436/170
[58] Field of Search .................. 422/56–58; 436/169, 170; 435/805, 14, 28, 16, 21, 26

[56] References Cited

U.S. PATENT DOCUMENTS

| | | |
|---|---|---|
| 3,298,789 | 1/1967 | Mast . |
| 3,630,957 | 12/1971 | Rey et al. .................. 436/95 |
| 3,992,158 | 11/1976 | Przybylowicz et al. .......... 422/57 |
| 4,292,272 | 9/1981 | Kitajima et al. . |
| 4,587,099 | 5/1986 | Rothe et al. .................. 422/58 |
| 4,605,629 | 8/1986 | Lange et al. .................. 422/58 |
| 4,647,430 | 3/1987 | Zweig .................. 422/58 |
| 4,781,890 | 11/1988 | Arai et al. .................. 422/57 |
| 4,816,224 | 3/1989 | Vogel et al. .................. 422/56 |

FOREIGN PATENT DOCUMENTS

| | | |
|---|---|---|
| 0113896 | 7/1984 | European Pat. Off. . |
| 0114403 | 8/1984 | European Pat. Off. . |
| 0207360 | 1/1987 | European Pat. Off. . |
| 0256806 | 2/1988 | European Pat. Off. . |
| 0272407 | 6/1988 | European Pat. Off. . |
| 3029301 | 2/1981 | Fed. Rep. of Germany . |
| 1933800 | 9/1974 | Japan . |
| 53-21677 | 7/1978 | Japan . |
| 55-164356 | 12/1980 | Japan . |
| 56-24576 | 3/1981 | Japan . |
| 63-101757 | 5/1988 | Japan . |

*Primary Examiner*—Jill A. Johnston
*Attorney, Agent, or Firm*—Birch, Stewart, Kolasch & Birch

[57] ABSTRACT

A device for colorimetric assay of at least one component in a liquid sample, which device comprises a support, a reagent layer formed on a part of one surface of the support and a sample-receiving layer which covers at least a part of the reagent layer and at least a part of the support surface, with which the timing of application of a sample on the device is automatically detected with accuracy.

14 Claims, 2 Drawing Sheets

DEVICE FOR ASSAY OF LIQUID SAMPLE

This is a continuation of application Ser. No. 07/675,049, filed Mar. 25, 1991 and now abandoned, which in turn is a continuation of application Ser. No. 07/442,635, filed Nov. 29, 1989 and now abandoned.

BACKGROUND OF THE INVENTION

1. Field of the Invention

The present invention relates to a device for assay of a liquid sample, and more particularly, to a dry type device for colorimetric assay of at least one component in a liquid sample, for example, body fluids such as blood.

2. Description of the Related Art

Assay of body fluids such as blood has been done in hospitals or by assay experts. Recently, with the development of a dry type assay device, a patient can carry out the assay easily, quickly and precisely. For example, the patient samples a small amount of his or her blood and determines the glucose content in the blood so as to control the sugar content in his or her food.

Typical examples of the dry type assay devices are disclosed in U.S. Pat. Nos. 3,298,789 and 3,630,957 and Japanese Patent Publication No. 33800/1974. With the device of the U.S. Patent, the sampled whole blood is placed on a reagent pad covered with an ethylcellulose layer. After a predetermined period of time, the blood sample is washed out with water, and the developed color of the reagent pad is detected. If erythrocytes remain on or in the reagent pad, they interfere with the detection of the developed color. To avoid such interference, the cellulose layer is provided to prevent penetration of the erythrocytes into the reagent pad and to facilitate removal of the erythrocytes. With the device of the above Japanese Patent Publication, a reagent pad comprises a water-resistant film which prevents penetration of the erythrocytes into the reagent pad.

Various special equipment has been developed and used in order to simplify the control of time for the assay and determination of the degree of developed color by the patient and also to increase the reliability of data. With such equipment, the patient punctures a blood vessel and then he or she should start a time control means of the equipment at the same time as he or she applies a drop of blood on a reagent layer of the assay device such as an assay stick.

However, it requires some skill to start the time control means and to apply the drop of blood on the reagent layer simultaneously. In most cases, just after the application of the drop of blood on the reagent layer, the patient starts the time control means. Therefore, the reliability of the data is not satisfactory. Further, it is troublesome for the patient to apply the drop of blood and to start the time control means simultaneously. In addition, the patient should wipe out the blood after a predetermined period of time from the application of blood and then set the assay device in the measuring equipment. Such procedures are troublesome for the patient and deteriorate the reliability of the data.

Among the above problems, troublesome wiping of the blood can be neglected by the assay devices disclosed in U S. Pat. No. 3,992,158, DE-A-3 029 301, Japanese Patent Publication Nos. 21677/1978 and 164356/1980 and Japanese Patent Kokai Publication No. 24576/1981. For example, the device disclosed in U.S. Pat. No. 3,992,158 is a multi-layer integral assay element comprising a transparent support, a reagent layer and a porous spreading layer which are laminated successively. In use, when the sample is applied on a spot of the spreading layer, it spreads in a transverse direction and migrates into the reagent layer to develop the color in the reagent layer. Then, the degree of color development is observed through the transparent support. With such device, the color development is measured without the removal of the applied blood. However, such device cannot overcome the problem that the control of time should be started simultaneously with the application of blood.

To avoid the troublesome time control, EP-A-256 806 and Japanese Patent Kokai Publication No. 101757/1988 disclose an equipment which can measure the blood color and the developed color with two beams of light having different wavelengths, one of which is absorbed by the erythrocytes and the other of which by the developed color from an opposite side to the sample applied side. In measurement, a drop of blood is applied on the reagent layer of the dry type assay device as shown in FIG. 1 which is set in the measuring equipment. That is, when the drop of blood is applied on the reagent layer 2 supported by a support 1 of the dry type assay device, reflectance of the light having the wavelength which is absorbed by the erythrocytes decreases, and the start of such decrease of reflectance is automatically detected by the equipment and regarded as the application of blood on the dry type assay device.

However, this type of equipment has the drawback that it tends to be influenced by stray light. That is, in this equipment, the application of sample and the degree of color development are both measured as changes of amounts of reflected lights at the same point indicated by the arrow C in FIG. 1. The timing of the sample application is detected as the change of amount of reflected light when the sample is applied. In general, the reflectance of light is expressed in terms of a percentage of the amount of light reflected on the reagent layer to the amount of light reflected on a standard white plate of magnesium oxide. With this equipment, since the amount of light from the reagent should be measured on the opposite side to the side which is illuminated with the measuring light, the reagent layer is transparent to some extent, and therefore, the amount of light received by light receiving means of the equipment is a sum of the light reflected by the reagent section and light from ambient light sources (e.g. the sun or room lamps) which passes through the reagent section and reaches the light receiving means. In measurement with this equipment, particularly when the room is light, as a finger reaches the reagent layer to apply the blood, the surface of reagent layer is shadowed with the finger. Then, even if the blood is not actually applied on the reagent layer, the reflectance is changed so that the timing of the start of measurement may not be correctly detected. In addition, this equipment may have an insufficient dynamic range, since the application of the sample and the degree of color development are both measured by the measurement of reflectance on the reagent layer, so that the degree of color development is measured by using the reflectance of the reagent layer including the blood as a background. Since the blood absorbs not only light at a specific wavelength but also light from the developed color and further light outside the visible light range, when the reflected light is measured against the erythrocyte component as the background, the decrease of optical dynamic range cannot be avoided. The decrease of optical dynamic range decreases the accuracy of measurement. The transparency of the reagent layer which is necessary for the detection of application of the sample is one of the causes for the decrease of dynamic range.

SUMMARY OF THE INVENTION

One object of the present invention is to provide an assay device which can determine the application timing of the sample on the device without malfunction.

Another object of the present invention is to provide an assay device which has a sufficient optical dynamic range.

Accordingly, the present invention provides a device for colorimetric assay of at least one component in a liquid sample, which device comprises a support, a reagent layer formed on a part of one surface of the support and a sample-receiving layer which covers at least a part of the reagent layer and at least a part of the support surface.

DETAILED DESCRIPTION OF THE DRAWINGS

Figure 1:
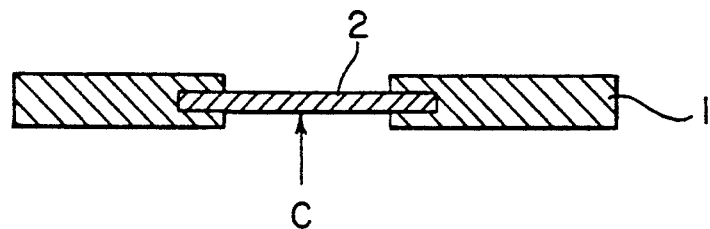
FIG. 1 is a cross section of one of the conventional assay devices.
Figure 2:
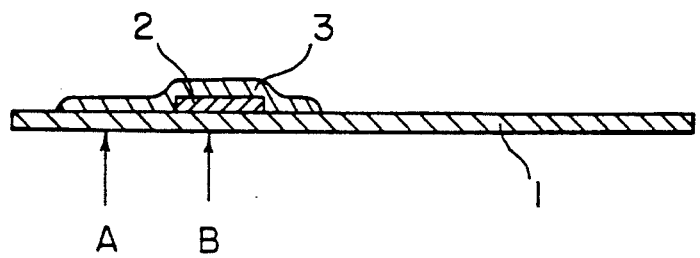
FIG. 2 is a cross section of one embodiment of the assay device of the present invention.

A basic assay device of the present invention is shown in FIG. 2. This device comprises a support 1 made of, for example, a transparent plastic strip. On one surface of the support 1, a reagent layer 2 is directly formed, and a sample-receiving layer 3 is provided to cover the reagent layer 2 and a part of the surface of the support 1. The sample-receiving layer 3 does not necessarily cover the whole area of the reagent layer 2.

The reagent layer 2 contains at least one reagent which reacts with the component to be analyzed in the liquid sample to develop a specific color and optionally a light reflecting agent which serves as a background.

Examples of the component to be analyzed are biochemical items in clinical tests such as glucose, galactose, urea nitrogen, uric acid, creatinine, ammonia, total proteins, albumin, lactic acid, glutamic-pyruvic transaminase, glutamic-oxaloacetic transaminase, alkaline phosphatase, lactate dehydrogenase, triglyceride, cholesterol, phospholipid, ketone body, bilirubin, hemoglobin and the like.

The reagents which react with the respective components are well known. For example, in case of analysis of glucose, a combination of glucose oxidase, peroxidase and ortho-toluidine is used. Since ortho-toluidine turns blue in a degree corresponding to the amount of glucose, the degree of developed blue color is measured to determine the amount of glucose. When the ketone body is analyzed, as disclosed in Japanese Patent Publication No. 38199/1988, a combination of beta-hydroxybutyric dehydrogenase, nicotinamide adenine dinucleotide, diaphorase and phenadine methosulfate is used. With such combination, among the ketone body, beta-hydroxybutyric acid which is useful as a criteria for diabetes can be quantitatively measured.

Examples of the light-reflecting agent are metal oxides such as titanium dioxide, magnesium oxide, zinc oxide and the like. The light-reflecting agent is useful to remove the interfering materials such as blood cells when the sample migrates from the sample-receiving layer to the reagent layer.

Since the sample-receiving layer covers a part of the support directly as shown in FIG. 2, it enables one to detect the change of reflectance on said layer through only the support but not the reagent layer at a position of the support indicated by the arrow A in FIG. 2.

Since the timing of sample application is detected at a position apart from the reagent layer, the light can be sufficiently reflected at the reagent layer so that the sufficiently wide optical dynamic range can be achieved.

To receive the sample and spread it over the sample-receiving layer, the sample-receiving layer is preferably made of a hydrophilic porous material such as a filter paper, a fabric, a non-woven fabric, a mesh, and the like.

Several modifications of the assay device of the present invention can be contemplated.

Figure 3:
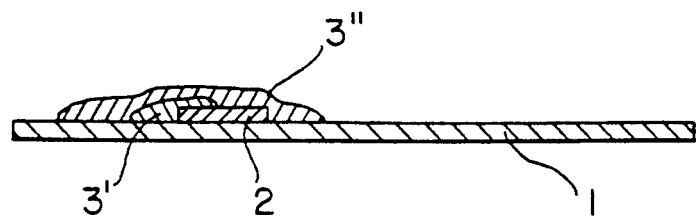
FIGS. 3 to 7 are cross sections of various modifications of the assay device of the present invention.

FIG. 3 is a cross section of the a modification. In this device, a part of the reagent layer 2 is covered with a porous material 3' and then covered with a mesh layer 3" which covers the whole area of the reagent layer 2 and a part of the support 1.

Figure 4:
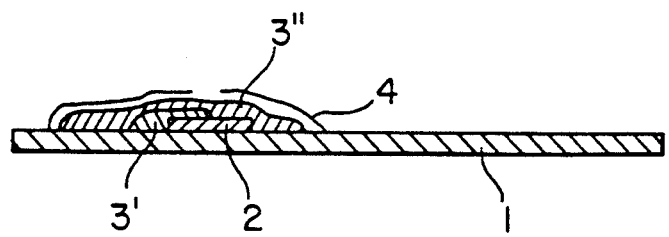

FIG. 4 is a cross section of a further modification of the device of FIG. 3. In this device, a covering 4 is provided over the mesh layer 3".

Figure 5:
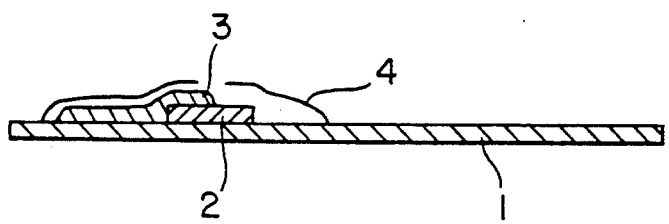
Figure 6:
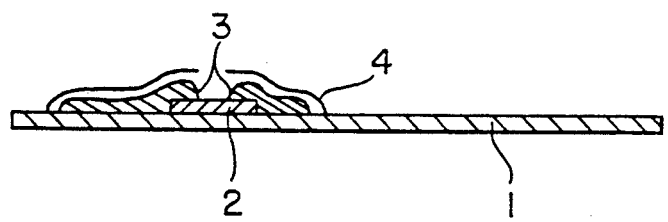

FIG. 5 is a cross section of a second modification. In this device, the sample-receiving layer 3 covers a part of the reagent layer 2 and a part of the support, and a covering 4 is provided over the reagent layer 2 and the sample-receiving layer 3. The device of FIG. 5 can be further modified as shown in FIG. 6.

Figure 7:
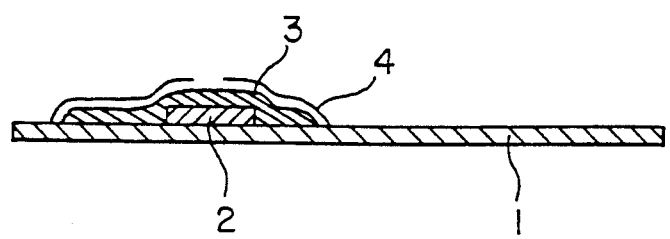

FIG. 7 is a modification of the basic device of FIG. 2 and has a covering 4.

How to carry out the measurement with the use of the assay device of the present invention will be illustrated.

As explained above, FIG. 2 shows a basic embodiment of the assay device of the present invention. In this device, the sample-receiving layer 3 covers the whole area of the reagent layer 2 and also a part of the support directly. The size of the thickness direction is enlarged for easy understanding.

In measurement, the assay device is set in the assay equipment. The equipment has two sets of reflectance measuring mechanisms, one of which measures directly the reflectance on the sample-receiving layer 3 at the position indicated by the arrow A and the other of which measures the reflectance on the reagent layer 3 at the position indicated by the arrow B.

When the sample is dropped on the sample-receiving layer 3, it spreads over the whole area of said layer 3. Then, the reflectance over the position indicated by the arrow A changes, and such reflectance change is measured by the reflectance measuring mechanism to detect the application of sample. From such reflectance change, time is counted. After a predetermined period of time, the reflectance at the position indicated by the arrow B is measured. When the covering is provided over the reagent layer as shown in FIGS. 4, 5, 6 and 7, the influence of stray light can be minimized. The covering may be made of a liquid-impermeable material. The measured reflectance is converted to the concentration of the particular component by using a calibration line which is beforehand produced.

What is claimed is:

1. A device for colorimetric assay of at least one component in a liquid sample, which device comprises:
   a transparent support,
   a reagent layer formed on a part of one surface of the support wherein the reagent layer contains at least one reagent which reacts with a component in a sample to be analyzed to develop a specific color which is measured colorimetrically, and
   a sample-receiving layer which covers at least a part of the reagent layer and at least a part of the support surface adjacent said reagent layer, wherein the sample-receiving layer comprises a porous material portion of filter paper, woven fabric or non-woven fabric which covers part of said support and part of said reagent layer, and comprises a mesh portion which covers said porous material portion, said reagent layer and said support, whereby the timing of the sample application onto the device is accurately determined by directly comparing the reflectance of said sample-receiving layer with the reflectance of the reagent layer.

2. The device according to claim 1, wherein the reagent contained in said reagent layer comprises glucose oxidase, peroxidase and ortho-toluidine.

3. The device according to claim 1, wherein the sample-receiving layer covers the whole area of the reagent layer.

4. The device according to claim 3, which further comprises a covering which covers the sample-receiving layer for minimizing the influence of stray light.

5. The device according to claim 1, wherein the support is a transparent plastic strip.

6. The device according to claim 1, wherein the reagent contained in said reagent layer reacts with a component in the sample to be analyzed, said component being selected from the group consisting of glucose, galactose, urea nitrogen, uric acid, creatinine, ammonia, total proteins, albumin, lactic acid, glutamic-pyruvic transaminase, glutamic-oxaloacetic transaminase, alkaline phosphatase, lactate dehydrogenase, triglyceride, cholesterol, phospholipid, ketone body, bilirubin and hemoglobin.

7. The device according to claim 1, wherein said porous material portion of said sample-receiving layer is made of a hydrophilic porous material.

8. A device for colorimetric assay of at least one component in a liquid sample, which device comprises:
   a transparent support,
   a reagent layer formed on a part of one surface of the support wherein the reagent layer contains at least one reagent which reacts with a component in a sample to be analyzed to develop a specific color which is measured colorimetrically and contains a light reflecting agent, and
   a sample-receiving layer which covers at least a part of the reagent layer and at least a part of the support surface adjacent said reagent layer, wherein the sample-receiving layer comprises a porous material portion of filter paper, woven fabric or non-woven fabric which covers part of said support and part of said reagent layer, and comprises a mesh portion which covers said porous material portion, said reagent layer and said support, whereby the timing of the sample application onto the device is accurately determined by directly comparing the reflectance of said sample-receiving layer with the reflectance of the reagent layer.

9. The device according to claim 8, wherein the reagent contained in said reagent layer comprises glucose oxidase, peroxidase and ortho-toluidine.

10. The device according to claim 8, wherein the light reflecting agent is a metal oxide.

11. The device according to claim 10, wherein said metal oxide is titanium dioxide, magnesium oxide or zinc oxide.

12. A device for colorimetric assay of at least one component in a liquid sample, which device comprises:
   a support;
   a reagent layer formed on a part of one surface of the support wherein the reagent layer contains at least one reagent which reacts with a component in a sample to be analyzed to develop a specific color which is measured colorimetrically;
   a sample-receiving layer which covers at least a part of the reagent layer and at least a part of the support surface adjacent said reagent layer, wherein the sample-receiving layer is formed from a material which facilitates change of light reflectance by the sample (1) through the support and the sample-receiving layer and (2) through the support and the reagent layer, wherein the timing of the sample application onto the device is accurately determined since the reflectance of the sample-receiving layer may be changed, wherein said sample-receiving layer covers said reagent layer so as to provide for an exposed central area of said reagent layer; and
   a covering which covers the reagent layer and the sample-receiving layer for minimizing the influence of stray light.

13. A device for colorimetric assay of at least one component in a liquid sample, which device comprises:
   a support,
   a reagent layer formed on a part of one surface of the support wherein the reagent layer contains at least one reagent which reacts with a component in a sample to be analyzed to develop a specific color which is measured colorimetrically,
   a sample-receiving layer which covers at least a part of the reagent layer and at least a part of the support surface adjacent said reagent layer, wherein the sample-receiving layer is formed from a material which facilitates change of light reflectance by the sample (1) through the support and the sample-receiving layer and (2) through the support and the reagent layer, wherein the timing of the sample application onto the device is accurately determined since the reflectance of the sample-receiving layer may be changed, and
   wherein said sample-receiving layer is made of a member selected from the group consisting of filter paper, woven fabric, non-woven fabric and mesh.

14. A device for colorimetric assay of at least one component in a liquid sample, which device comprises:
   a support,
   a reagent layer formed on a part of one surface of the support wherein the reagent layer contains at least one reagent which reacts with a component in a sample to be analyzed to develop a specific color which is measured colorimetrically,
   a sample-receiving layer which covers at least a part of the reagent layer and at least a part of the support surface adjacent said reagent layer, wherein the sample-receiving layer is formed from a material which facilitates change of light reflectance by the sample (1) through the support and the sample-receiving layer and (2) through the support and the reagent layer, wherein the timing of the sample application onto the device is accurately determined since the reflectance of the sample-receiving layer may be changed, and a covering which covers the reagent layer and the sample receiving layer for minimizing the influence of stray light, wherein said sample-receiving layer covers said reagent layer so as to provide for an exposed central area of said reagent layer.

* * * * *